United States Patent [19]  [11] 4,371,542
Beck et al.  [45] Feb. 1, 1983

[54] HETERO-IMINO-PROSTACYCLINS

[75] Inventors: Gerhard Beck, Frankfurt am Main; Jochen Knolle, Kriftel; Richard H. Rupp, Frankfurt am Main; Bernward Schölkens, Kelkheim, all of Fed. Rep. of Germany

[73] Assignee: Hoechst Aktiengesellschaft, Frankfurt am Main, Fed. Rep. of Germany

[21] Appl. No.: 236,634

[22] Filed: Feb. 20, 1981

[30] Foreign Application Priority Data

Feb. 23, 1980 [DE] Fed. Rep. of Germany ....... 3006865

[51] Int. Cl.³ .................... C07D 209/52; A61K 31/40
[52] U.S. Cl. ..................................... 424/274; 548/452; 548/465; 548/512; 542/429; 542/430; 542/468; 542/471; 542/472; 549/307
[58] Field of Search ................... 260/326.27, 326.5 B, 260/326.5 SM, 326.5 S; 424/274; 542/468, 471, 472, 429, 430

[56] References Cited

U.S. PATENT DOCUMENTS 4,097,489  6/1978  Bundy ........................... 260/326.27
4,151,176  4/1979  Bundy ........................... 260/326.27
4,161,584  7/1979  Bundy ........................... 260/326.27
4,234,597  11/1980  Hayashi et al. ................ 260/326.27

Primary Examiner—Mary C. Lee
Attorney, Agent, or Firm—Curtis, Morris & Safford

[57] ABSTRACT

What are disclosed are prostacylin $PGI_2$ analogs of the formula

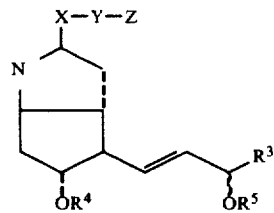

having a more specific or longer lasting pharmacological action than $PGI_2$, methods of making these analogs; and methods and pharmaceutical preparations for inhibiting blood platelet aggregation, for treating hypertension, for the treatment or prophylaxis of gastrointestinal ulcers, and for the treatment of asthma.

9 Claims, No Drawings

HETERO-IMINO-PROSTACYCLINS

Prostacyclin PGI$_2$, a recently isolated natural substance from the family of the prostaglandins, is distinguished by its very pronounced thrombocyte aggregation-inhibiting properties (The Lancet 1977, 18). Moreover, PGI$_2$ is capable of relaxing certain blood vessels, for example coronary arteries [Prostaglandins 13, 3, 1977], so that it can be used for the therapy and prophylaxis of thromboses and infarctions. PGI$_2$ also shows a pronounced hypotensive action [for example IRCS Med. Sci. 6, 392 (1978)].

The present invention relates to new analogs of PGI$_2$ of the general formula I

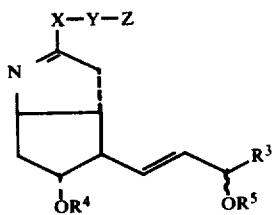

which have a more specific action and/or a longer period of action than PGI$_2$ and in which:

X is an oxygen or sulfur atom or an NH group,

Y is a straight-chain or branched alkylene radical having up to eight carbon atoms, a straight-chain or branched unsaturated aliphatic radical having three to eight carbon atoms, a cycloaliphatic radical having three to six carbon atoms or a phenylene radical, Z is a radical of the formula —CO$_2$R$^1$, —CH$_2$OH or CH$_2$N(R$^2$)$_2$, wherein R$^1$ is hydrogen, a straight-chain or branched alkyl radical having up to 8 carbon atoms, a straight-chain or branched unsaturated aliphatic hydrocarbon radical having three to six carbon atoms, a cycloaliphatic hydrocarbon radical having three to seven carbon atoms, an araliphatic hydrocarbon radical having seven to nine carbon atoms or a physiologically acceptable metal ion, NH$_4$ ion or an ammonium ion derived from a primary, secondary or tertiary amine, or a tetraalkylammonium ion, R$^2$ is hydrogen or a straight-chain or branched aliphatic hydrocarbon radical having up to five C atoms, or R$^2$-R$^2$ conjointly are a —(CH$_2$)$_n$ group with n=3-6, R$^3$ is an aryl radical which can be monosubstituted to trisubstituted in the nucleus by halogen, trifluoromethyl and/or alkyl or alkoxy each having 1-6 C atoms, or a cycloaliphatic radical having 3-8 carbon atoms or a straight-chain or branched alkyl radical having up to eight carbon atoms or a straight-chain or branched unsaturated aliphatic hydrocarbon radical having three to eight carbon atoms, which radicals can in turn be substituted by (a) a straight-chain or branched alkoxy radical having up to six carbon atoms or a straight-chain or branched alkenyloxy or alkynyloxy radical having three to six carbon atoms, (b) halogen, phenyl or an α- or β-thienyl or α- or β-furyl radical which in turn can be monosubstituted to trisubstituted in the nucleus by halogen, trifluoromethyl and/or alkyl or alkoxy each having 1-6 C atoms, or (c) a phenoxy radical, an α- or β-thienyloxy radical or a cycloalkoxy radical having 3-7 carbon atoms, it being possible for the said radicals to be in turn monosubstituted to trisubstituted in the nucleus by halogen, trifluoromethyl and/or alkyl or alkoxy having 1-6 C atoms, and R$^4$ and R$^5$ are each hydrogen or a protective group which can readily be eliminated under neutral or basic conditions.

Amongst the substituents R$^1$, the following are preferred:

hydrogen, straight-chain or branched alkyl having up to 8 C atoms, a straight-chain or branched unsaturated hydrocarbon radical having up to 4 C atoms, a cycloaliphatic hydrocarbon radical having 5–7 C atoms, an araliphatic hydrocarbon radical having 8 or 9 C atoms or an ammonium ion derived from a primary, secondary or tertiary amine, in particular:

hydrogen, methyl, ethyl, n-butyl, n-pentyl, n-hexyl, n-heptyl, 2-propyl, 2-butyl, 2-pentyl, 3-hexyl, 2-methylpropyl, 2-methylbutyl, 4,4-dimethylpentyl, 5,5-dimethylhexyl, cyclopentyl, cyclohexyl, cycloheptyl, methylammonium, dicyclohexylammonium and tris-(hydroxymethyl)-methylammonium.

Amongst the substituents R$^3$, those listed below are particularly preferred:

unsubstituted phenyl or phenyl monosubstituted by halogen, trifluoromethyl, C$_{1-4}$-alkyl or C$_{1-4}$-alkoxy, straight-chain or branched C$_{3-7}$-alkyl which can be substituted by C$_{5-7}$-cycloalkyl, by C$_{1-3}$-alkoxy, by phenoxy or halogenophenoxy, by thienyloxy or halogenothienyloxy, by cyclohexyloxy, by thienyl, by halogenothienyl or by furyl, all of which substituents may be substituted further, in particular:

n-pentyl, 1,1-dimethylpentyl, cyclopentylmethyl, cyclohexylmethyl, 1,1-dimethyl-2-ethoxy-ethyl, 1,1-dimethyl-2-methoxy-ethyl, 1,1-dimethyl-cyclohexyloxymethyl, 1-fluoropentyl, 1-chloropentyl, 5-fluoropentyl, 5-chloropentyl,2-(thien-3-yl)-ethyl, 2-(thien-2-yl)-ethyl, 2-(2-chloro-thien-3-yl)-ethyl, 2-(5-chloro-thien-2-yl)-ethyl, phenoxymethyl, 3-chlorophenoxymethyl, thien-2-yl-oxymethyl, 2-chloro-thien-3-yl-oxymethyl, 5-chloro-thien-2-yl-oxymethyl, 2-(fur-3-yl)-ethyl, 2-(fur-2-yl)-ethyl, 2-(2,2,3,3-tetrafluorocyclobutyl)-ethyl, phenyl, 3-chlorophenyl and 3-trifluoromethyl-phenyl.

Amongst the substituents Y, those listed below are particulary preferred:

ethylidene, trimethylene, methyltrimethylene, methyltetramethylene, propenylene, cyclobutenylene, cyclopentenylene and phenylene.

The invention also relates to a process for the manufacture of prostacyclin derivatives of the formula I, which comprises (a) reacting the alcohol of the formula II

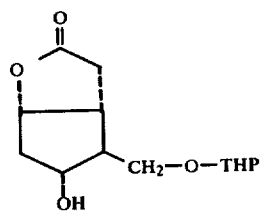

wherein THP denotes the tetrahydropyranyl radical, to give the benzyl ether of the formula III

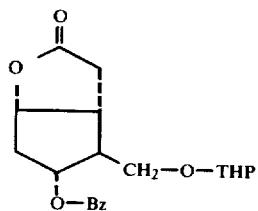

wherein Bz denotes the benzyl radical, (b) opening the lactone of the formula III by means of ammonia to give the hydroxyamide of the formula IV

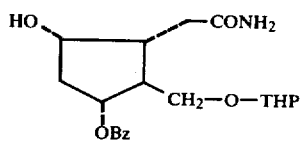

(c) oxidizing the hydroxyl functional group in the alcohol of the formula IV to give the ketone of the formula V

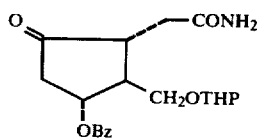

(d) isomerizing the ketoamide of the formula V to give the hydroxylactam of the formula VI

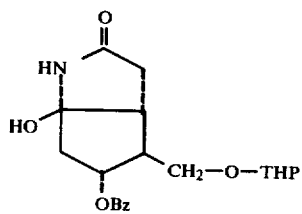

(e) reacting the hydroxylactam of the formula VI, the ketoamide of the formula V or a mixture of the hydroxylactam of the formula VI and the ketoamide of the formula V with a mercaptan of the formula VII $R^6$—SH                    VII in which $R^6$ is an alkyl radical having 1–5 C atoms or a phenyl radical, to give a thioether of the formula VIII

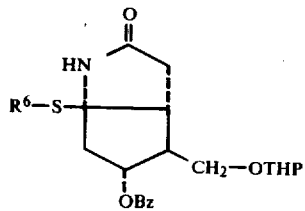

wherein $R^6$ has the meanings given under the formula VII, (f) eliminating the radical —$SR^6$ in the thioether of the formula VIII by reduction, a lactam of the formula IX

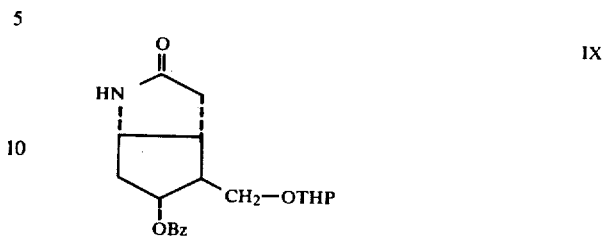

being obtained, (g) splitting off the benzyl ether group in the lactam of the formula IX by hydrogenation, a hydroxylactam of the formula X

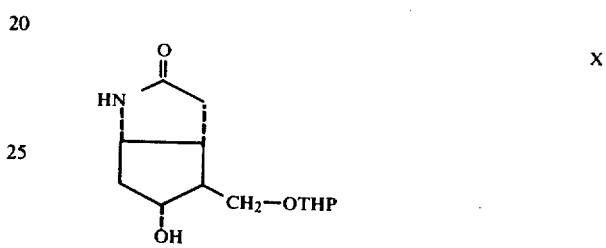

being obtained, or (g') carrying out the elimination of the group —$SR^6$ and of the benzyl ether group in one step, (h) protecting the hydroxyl functional group in the lactam of the formula X by a group which can be eliminated again under neutral or basic conditions, whereby a lactam of the formula XI

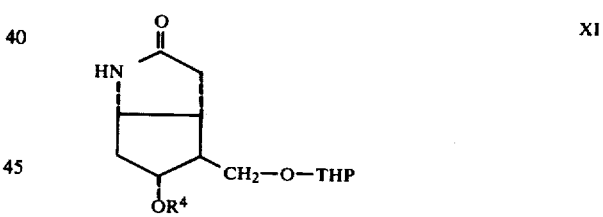

is obtained, wherein $R^4$ is a protective group which can readily be eliminated under neutral or basic conditions, (i) eliminating the THP group in the lactam of the formula XI by selective hydrolysis, an alcohol of the formula XII

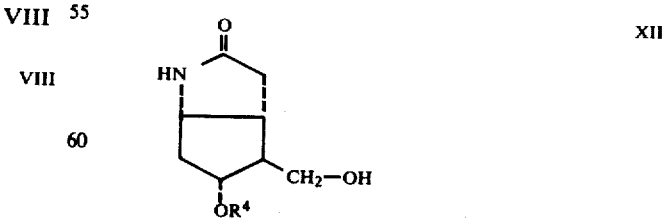

being obtained, wherein $R^4$ has the meaning given under the formula XI, (j) oxidizing the alcohol of the formula XII to the aldehyde of the formula XIII

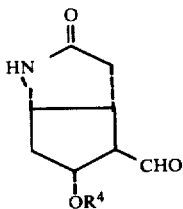

wherein $R^4$ has the meaning given under the formula XI, (k) reacting the aldehyde of the formula XIII with a phosphonate of the formula XIV

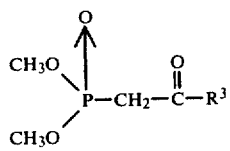

wherein $R^3$ has the meanings given under the formula I, to give an enone of the formula XV

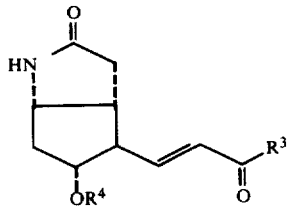

wherein $R^4$ has the meanings given under the formula XI and $R^3$ has the meanings given under the formula I, (l) reducing the enone of the formula XV in a known manner by means of a suitable reducing agent to give a mixture of epimers of the alcohols of the formula XVI

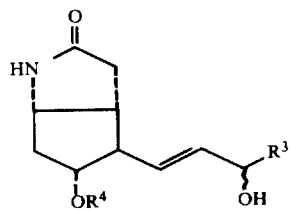

wherein $R^3$ has the meanings given under the formula I and $R^4$ has the meanings given under the formula XI, (m) protecting the alcohol functional group in the alcohols of the formula XVI by a group which can be eliminated again under neutral or basic conditions, whereby compounds of the formula XVII

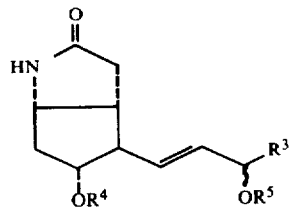

are obtained, in which $R^3$ has the meanings given under the formula I, $R^4$ has the meaning given under the formula XI and $R^5$ is a protective group which can readily be eliminated under neutral or basic conditions, it being possible for $R^4$ and $R^5$ to be identical or different, (n) converting the lactams of the formula XVII by conventional methods into the thiolactams of the formula XVIII

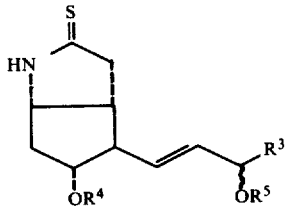

wherein $R^3$ has the meaning given under the formula I and $R^4$ and $R^5$ have the meaning given under the formula XVII, (o) alkylating the thiolactams of the formula XVIII with alkyl halides of the formula XIX $$Z-Y-Hal \qquad XIX$$

wherein Hal is iodine, chlorine or bromine and Y and Z have the meanings given under the formula I, thiolactim ethers of the formula XX

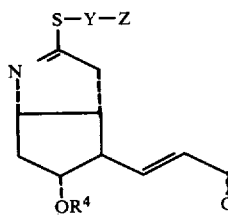

being obtained, wherein Y, Z and $R^3$ have the meanings given under the formula I and $R^4$ and $R^5$ have the meanings given under the formula XVII, (p) eliminating the protective groups of the alcohol functional groups in the compounds of the formula XX by a hydrolysis with basic catalysis, whereby compounds of the formula I are obtained, wherein X is sulfur, or (q) alkylating the lactams of the formula XVII with alkyl halides of the formula XIX, lactim ethers of the formula XXI

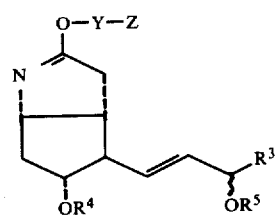

being obtained, wherein Y, Z and $R^3$ have the meanings given under the formula I and $R^4$ and $R^5$ have the meaning given under the formula XVII, (r) eliminating the protective groups on the alcohol functional groups in the compounds of the formula XXI by a hydrolysis with basic catalysts, whereby compounds of the formula I are obtained, wherein X is oxygen, or (s) converting the thiolactams of the formula XVIII into the alkyl thiolactim ethers of the formula XXII

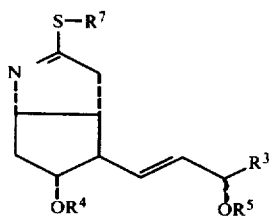

XXII wherein R³ has the meanings given under the formula I and R⁴ and R⁵ have the meanings given under the formula XVII, and R⁷ is a methyl or ethyl group, (t) reacting the thiolactim ethers of the formula XXII with amines of the formula XXIII

Z—Y—NH₂       XXIII wherein Z and Y have the meanings given under the formula I, to give amidines of the formula XXIV

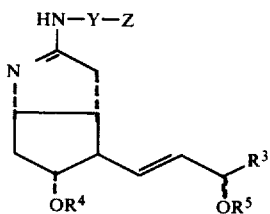

XXIV wherein Y, Z and R³ have the meanings given under the formula I and R⁴ and R⁵ have the meanings given under the formula XVII, (u) eliminating the protective groups on the alcohol functional groups in the compounds of the formula XXIV by a hydrolysis with basic catalysis, whereby compounds of the formula I are obtained, wherein X is NH, (v) if appropriate, saponifying compounds of the formula XX, XXI and XXIV, wherein R⁴ and R⁵ are hydrogen and wherein Z is alkoxycarbonyl, to give compounds of the formula I, wherein R³, X and Y have the meanings given under the formula I and Z is carboxyl or a cation, (w) if appropriate, esterifying a compound of the formula I, wherein Z is carboxyl or a cation and R², X and Y have the meanings given under the formula I, to give a compound of the formula I, wherein R¹ is an alkyl radical having the meaning given under the formula I and R³, X and Y have the meanings given under the formula I, and/or (y) if appropriate, in a compound of the formula I, wherein Z is carboxyl or a physiologically acceptable metal ion, NH₄ ion or an ammonium ion which is derived from a primary, secondary or tertiary amine, and R¹, X and Y have the meanings given under the formula I, exchanging the cation R¹ for another cation.

The preparation of the alcohol II used as the starting material in the process according to the invention can be carried out analogously to the process described in J. Am. Chem. Soc. 95, 7522 (1973).

The preparation of the benzyl ether is carried out by conventional methods, by reacting the alcohol of the formula II in inert solvents, such as, for example, dimethylformamide, dimethoxyethane or toluene, with benzyl bromide in the presence of bases, such as, for example, sodium hydride, barium hydroxide or potassium carbonate, at temperatures of 20°-140° C. It is, however, also possible to omit the inert solvent and to let the reaction proceed in benzyl bromide.

The lactone of the formula III can be reacted with ammonia, for example in alcoholic solution at an elevated temperature (70°-130° C.), to give the hydroxyamide of the formula IV. This reaction is expediently carried out in an autoclave. At this point, it is advantageous to purify the product by chromatography over silica gel.

The oxidation of the hydroxyamide, thus obtained, of the formula IV to give the ketoamide of the formula V can be carried out with oxidizing agents, such as chromium trioxide/dimethyl sulfate, chromium trioxide/pyridine, pyridinium chlorochromate, pyridinium dichromate or chromium trioxide/sulfuric acid/water, in inert solvents, such as dimethylformamide, methylene chloride or acetone, at temperatures of −30° to 40° C., preferably between −25° and −20° C. At this point, the ketoamide of the formula V can be purified by chromatography over silica gel.

The ketoamide of the formula V is in tautomeric equilibrium with its cyclic isomer, that is to say the hydroxylactam of the formula VI. Such equilibria are known from the literature, for example from Chem. Ber. 103, 3205 (1970).

When the ketoamide of the formula V is dissolved in an inert solvent, for example acetone, methanol, ethanol, tetrahydrofuran, chloroform or methylene chloride, and the solution is left to stand at 20°-40° C., the hydroxylactam of the formula VI is obtained.

The hydroxylactam of the formula VI, the ketoamide of the formula V or mixtures of the two can be reacted with mercaptans of the formula VII and chlorotrimethylsilane in inert solvents, such as, for example, methylene chloride, chloroform, toluene or dimethoxyehtane, to give thioethers of the formula VIII. The reaction is carried out at 30° to 100° C., advantageously in the presence of an organic base, such as, for example, pyridine, triethylamine or 1,4-diazabicyclo[4,3,0]non-5-ene (DBN).

The reduction of the thioethers of the formula VIII is effected by reaction with a metal catalyst, such as, for example, Pd/C, Raney Ni or NiCl₂/NaBH₄, and hydrogen in a lower alkanol, such as, for example, methanol, ethanol, t-butanol or isopropanol, or in acetone.

The benzyl ether of the formula IX is obtained by heating.

The benzyl ether of the formula IX can then be reacted with the same catalysts as described for the reaction of the thioethers of the formula VIII and with hydrogen in a lower alkanol, for example methanol, i-propanol or butanol, THF or ethyl acetate to give the alcohol of the formula X. 5–10% of a mineral acid, for example concentrated hydrochloric acid, or of an organic acid, such as, for example, acetic acid, can here be added to the inert solvent. This can be effected under normal pressure and at room temperature, or the reaction can be carried out in an autoclave at 20°-80° C. under a pressure of 50–100 atmospheres.

It is, however, also possible to treat the thioethers of the formula VIII, at 20°-80° C., with a large excess of the catalysts described above and with hydrogen, the R⁶—S— grouping and the benzyl ether grouping being eliminated simultaneously and the alcohol of the formula X thus being obtained directly.

The preparation of the compounds of the formula XI is carried out by reacting the alcohol of the formula X either with anhydrides of the formula $R^4$—O—$R^4$ or with acid chlorides of the formula $R^4$—Cl, wherein $R^4$ represents an acyl group. Amongst acyl groups, the substituents listed below are particularly preferred:

acetyl, propionyl, benzoyl, substituted benzoyl (for example 3-methyl-benzoyl, 4-phenylbenzoyl, 2,4-dinitrobenzoyl, 2-nitrobenzoyl, 1-naphthoyl and 2-naphthoyl). In the case of the anhydrides, the reaction is carried out without a solvent or, in case of reaction with acid chlorides, it is carried out in inert solvents, such as, for example, chloroform, methylene chloride, carbon tetrachloride, tetrahydrofuran or dioxane, in the presence of a base. Examples of suitable bases are pyridine, triethylamine or 4-dimethylaminopyridine.

The tetrahydropyranyl group in compounds of the formula XI can be eliminated by an acid-catalyzed, selective hydrolysis. Suitable acids are dilute mineral acids or organic acids, such as, for example, p-toluenesulfonic acid, oxalic acid or acetic acid, the reaction being effected in inert solvents, such as methanol, ethanol, chloroform, methylene chloride, tetrahydrofuran or toluene, at 0°–50° C.

The oxidation of the alcohols of the formula XII to aldehydes of the formula XIII can be accomplished by means of oxidizing agents, such as pyridinium chlorochromate or pyridinium dichromate, in inert solvents, such as methylene chloride or chloroform. A further possible oxidation method comprises a reaction with thioanisole/$Cl_2$/trimethylamine in carbon tetrachloride. The aldehyde of the formula XIII is preferably processed further without additional purification.

Subsequently, the aldehydes of the formula XIII are reacted by the Horner-Emmons-Wittig method with the phosphonic acid esters of the formula XIV to give the unsaturated ketones of the general formula XV, a preferred embodiment comprising the preparation of the sodium salt of the phosphonic acid ester of the formula XIV, using sodium hydride in dimethoxyethane, the subsequent addition of the aldehyde of the formula XIII and a reaction period of 2–6 hours at room temperature. The phosphonic acid esters of the formula XIV are prepared by processes known from the literature [see, for example, J. Am. Chem. Soc. 88, 5654 (1966)].

The alcohols of the formula XVI are obtained in the form of mixtures of their epimers when the ketones of the formula XV are reduced with a complex metal hydride, preferably an alkali metal boranate, or with D,L-isobornyloxyaluminum isopropoxide.

The alcohol functional group in compounds of the formula XVI can be protected, analogously to the process described for the preparation of compounds of the formula XI, using the protective groups described there. Silyl protective groups can, however, also be used. For this purpose, the alcohol of the formula XVI is reacted in an inert solvent, such as, for example, chloroform, methylene chloride or toluene, at 0°–30° C. with the silyl chloride, preferably dimethyl-t-butylsilyl chloride, and a base. Examples of suitable bases are triethylamine, pyridine or 1,5-diazabicyclo[5,4,0]undec-5-ene (DBU).

The thiolactams of the formula XVIII can be prepared from the lactams of the formula XVII by reaction with sulfur-transferring reagents, such as, for example, phosphorus pentasulfide, phosphorus pentasulfide/calcium oxide, the phosphorus pentasulfide/pyridine complex or the phosphorus pentasulfide/anisole complex, in inert solvents, such as, for example, toluene, dimethoxyethane or pyridine, by methods known from the literature [see, for example, Bull. Soc. Chim. Belg. 87 (3), 229 (1978)].

For the preparation of the thiolactim ethers of the formula XX, the thiolactams of the formula XVIII are alkylated with alkyl halides of the formula XIX. This reaction is carried out in an inert solvent, such as, for example, toluene, tetrahydrofuran, dimethoxyethane or dimethylformamide, in the presence of bases, such as, for example, pyridine, triethylamine, potassium carbonate or sodium hydride, at 15°–55° C. A preferred embodiment of this reaction comprises the preparation of the sodium salt of the thiolactams of the formula XVIII using sodium hydride in dimethoxyethane, the dropwise addition thereto of the alkyl halide of the formula XIX in dimethoxyethane, and stirring at 25° C. for 2–6 hours.

The preparation of lactim ethers of the formula XXI is carried out by alkylating the lactams of the formula XVII with alkyl halides of the formula XIX in an inert solvent, such as benzene, toluene, dioxane or xylene, at temperatures from 80° to 160° C. in the presence of an inorganic base, preferably silver oxide or silver hydroxide.

To prepare the amidines of the formula XXIV, the thiolactam of the formula XVIII is alkylated to give a S-alkyl compound of the formula XXII. This can be carried out in the same way as the preparation of the thiolactim ethers of the formula XV, by initially preparing the sodium salt of the thiolactam, using sodium hydride in an inert solvent, such as dimethoxyethane, tetrahydrofuran or dioxane, and then reacting the product with an alkyl halide of the formula $R^7$-halogen, wherein $R^7$ is methyl or ethyl and halogen is iodine, bromine or chlorine, but preferably iodine. It is, however, also possible to react the thiolactam of the formula XVIII with the alkyl halide of the formula $R^7$-halogen in an inert solvent, such as acetone, ethyl acetate or chloroform, and to liberate the thiolactim ether of the formula XXII by means of bases, such as sodium bicarbonate, sodium carbonate or potassium carbonate.

The amidines of the formula XXIV are obtained by heating the thiolactim ethers of the formula XXII with amines of the formula XXIII in a lower alkanol, such as, for example, methanol or ethanol, or in an inert solvent, such as, for example, dioxane or acetone.

The protective groups $R^4$ and $R^5$ in the compounds of the formulae XX, XXI or XXIV can be eliminated under mild alkaline conditions, for example using sodium carbonate or potassium carbonate in alcoholic solution. This is carried out at −10° to +30° C., and compounds of the formula I are obtained.

Compounds of the formula I, wherein Z is an alkoxycarbonyl group, can be saponified in the conventional manner in an alkaline medium to give compounds of the formula I wherein Z is a carboxyl group, for example using NaOH or KOH in a low molecular weight alcohol, such as methanol, or an ether, such as dimethoxy ether or THF, if appropriate in the presence of water. Advantageously, an equimolar amount or a very small excess of alkali metal hydroxide is used, so that the alkali metal salt of the formula I ($R^1$=alkali metal ion) is obtained by evaporation of the solvent, preferably by freeze-drying.

The alkali metal cation can be exchanged for any other desired cations in the customary manner on ion exchangers. For this purpose, the solution of the alkali metal salt of a hetero-imino-prostacyclin derivative according to the invention is run through a column packed with a cation exchanger, such as, for example, Amberlite CG-50 or Dowex CCR-2.

The cation exchanger is charged with the desired cation, for example with an ammonium ion derived from a primary, secondary or tertiary amine. The desired salt is obtained by evaporation of the eluate.

Compounds of the formula I, in which Z is a carboxyl group and $R^1$ is $NH_4$ or an ammonium ion derived from a primary, secondary or tertiary amine, can also be prepared by adding an equimolar amount of the corresponding amine to compounds of the formula I, in which Z is carboxyl and $R^1$ is hydrogen, in an alcoholic solution and evaporating the solvent.

Compounds of the formula I, wherein Z is a carboxyl group or carboxylate group ($R^1$ = hydrogen or a cation) can be esterified to give compounds of the formula I, wherein $R^1$ is an alkyl radical. Thus, for example, a hetero-imino-prostacyclin derivative of the formula I ($R^1$ = H) can be esterified at temperatures between $-40°$ C. and $+20°$ C. with diazoalkanes of the formula $R^1 = N_2$ ($R^1$ = alkyl), it being possible to use the customary solvents, such as, for example, diethyl ether, tetrahydrofuran, chloroform or low molecular weight alcohols, such as methanol. The resulting esters can be isolated in a simple manner by evaporating the solvent and, if desired, they can be purified by chromatography. A preferred esterification method comprises reacting the salt of the corresponding hetero-imino-prostacyclin derivative I ($R^1$ = cation) with an alkylating agent $R^1 = Z'$ in a suitable solvent in the presence of a base, such as, for example, a metal alcoholate or metal carbonate. Examples of suitable metal alcoholates are sodium methylate, sodium ethylate or potassium tertiarybutylate, and examples of suitable carbonates are calcium carbonate or sodium bicarbonate. Suitable solvents which can be used are alcohols, such as, for example, methanol or tert.-butanol, ethers, such as tetrahydrofuran or 1,2-dimethoxy-ether, and in particular dipolar aprotic solvents, such as dimethylformamide, dimethyl sulfoxide, acetonitrile or N-methylpyrrolidone. In the alkylating agents $R^1$—$Z'$, $Z'$ preferably is bromine or iodine, or a sulfonic acid radical.

The compounds of the formula XVI can be employed in the subsequent reactions as a mixture of diastereomers with respect to the position of the hydroxyl groups on the carbon atom 15 (prostaglandin nomenclature), as pure α-isomers or β-isomers, or in the form of optically active antipodes. The separation of stereoisomers or the resolution of antipodes can, however, also be carried out after any susequent reaction stage. This means that all the reactions described can be carried out with mixtures of diastereomers, pure diastereomers or optically active antipodes. The claimed compounds of the formula 1 therefore comprise mixtures of diastereomers, pure diastereomers, mixtures of epimers and pure epimers.

If the individual reaction products are not already obtained in a form which is sufficiently pure for use in the subsequent reaction stage, purification by means of, for example, column chromatography, thin-layer chromatography or high-pressure liquid chromatography, is advisable.

In addition to the compounds described in the examples, the following further compounds can also be prepared by the processes according to the invention:

2-Aza-3-(1-aza-4-carboxybut-1-yl)-6-(3-(R,S)-hydroxy-3-cyclohexyl-propen-1-yl)-7-hydroxybicyclo[3.3.0]oct-2-ene 2-Aza-3-(1-aza-4-carboxybut-1-yl)-6-(3-(R,S)-hydroxy-6-oxa-octen-1-yl)-7-hydroxybicyclo[3.3.0]oct-2-ene 2-Aza-3-(1-aza-4-carboxybut-1-yl)-6-(3-(R,S)-hydroxy-4,4-dimethyl-octen-1-yl)-7-hydroxybicyclo[3.3.0]oct-2-ene 2-Aza-3-(1-aza-4-carboxybut-1-yl)-6-3-(R,S)-hydroxy-3-phenoxymethyl-propen-1-yl)-7-hydroxybicyclo[3.3.0]oct-2-ene 2-Aza-3-(1-aza-4-carboxybut-1-yl)-6-(3-(R,S)-hydroxy-3-(2,2,3,3-tetrafluorocyclobutylethyl)-propen-1-yl)-7-hydroxybicyclo[3.3.0]oct-2-ene 2-Aza-3-(1-aza-4-carboxybut-1-yl)-6-(3-(R,S)-hydroxy-3-(2-chlorothien-3-yloxymethyl)-propen-1-yl)-7-hydroxybicyclo[3.3.0]oct-2-ene 2-Aza-3-(4-carboxymethylanilino)-6-(3-(R,S)-hydroxy-3-cyclohexyl-propen-1-yl)-7-hydroxybicyclo[3.3.0]oct-2-ene 2-Aza-3-(4-carboxymethylanilino)-6-(3-(R,S)-hydroxy-6-oxa-octen-1-yl)-7-hydroxybicyclo[3.3.0]oct-2-ene 2-Aza-3-(4-carboxymethylanilino)-6-(3-(R,S)-hydroxy-4,4-dimethyl-octen-1-yl)-7-hydroxybicyclo[3.3.0]oct-2-ene 2-Aza-3-(4-carboxymethylanilino)-6-(3-(R,S)-hydroxy-3-phenoxymethyl-propen-1-yl)-7-hydroxybicyclo[3,3,0]oct-2-ene 2-Aza-3-(4-carboxymethylanilino)-6-(3-(R,S)-hydroxy-3-(2,2,3,3-tetrafluorocyclobutylethyl)-propen-1-yl)-7-hydroxybicyclo[3.3.0]oct-2-ene 2-Aza-3-(4-carboxymethylanilino)-6-(3-(R,S)-hydroxy-3-(2-chlorothien-3-yloxymethyl)-propen-1-yl)-7-hydroxybicyclo[3.3.0]oct-2-ene 2-Aza-3-(1-thia-4-carboxymethylbut-1-yl)-6-(3-(R,S)-hydroxy-6-oxa-octen-1-yl)-7-hydroxybicyclo[3.3.0]oct-2-ene 2-Aza-3-(1-thia-4-carboxymethylbut-1-yl)-6-(3-(R,S)-hydroxy-4,4-dimethyl-octen-1-yl)-7-hydroxybicyclo[3.3.0]oct-2-ene 2-Aza-3-(1-thia-4-carboxymethylbut-1-yl)-6-(3-(R,S)-hydroxy-3-phenoxymethyl-propen-1-yl)-7-hydroxybicyclo[3.3.0]oct-2-ene 2-Aza-3-(1-thia-4-carboxymethylbut-3-en-1-yl)-6-(3-(R,S)-hydroxy-4,4-dimethyl-octen-1-yl)-7-hydroxybicyclo[3.3.0]oct-2-ene 2-Aza-3-(1-thia-4-carboxymethylbut-3-en-1-yl)-6-(3-(R,S)-hydroxy-3-phenoxymethyl-propen-1-yl)-7-hydroxybicyclo[3.3.0]oct-2-ene 2-Aza-3-(1-oxa-4-carboxymethylbut-1-yl)-6-(3-(R,S)-hydroxy-4,4-dimethyl-octen-1-yl)-7-hydroxybicyclo[3.3.0]oct-2-ene 2-Aza-3-(1-oxa-4-carboxymethylbut-1-yl)-6-(3-(R,S)-hydroxy-3-phenoxymethyl-propen-1-yl)-7-hydroxybicyclo[3.3.0]oct-2-ene.

The products according to the invention, of the formula I, are highly active physiologically.

Thus, these compounds are active, for example, in the inhibition of blood platelet aggregation, in the reduction of the adhesive properties of the blood platelets and in the removal or prevention of thrombi in mammals, including humans. The substances can therefore be used for the treatment and prevention of myocardial infarctions, for the treatment and prevention of post-operative thrombi, for keeping implanted vessels open and for the treatment of diseases, such as arteriosclerosis, blood coagulation due to lipemia and other clinical conditions in which the underlying etiology is connected with a lipid disequilibrium or hyperlipidemia. Further in vivo uses in geriatric patients are the prevention of central ischemic failures and the long-term prophylaxis after myocardial infarctions and strokes. For this purpose, the compounds are administered systemically, for example intravenously, subcutaneously, intramuscularly or in the form of sterile implants for a more prolonged action. For a rapid action, intravenous administration is preferred. The daily doses used are about 0.15–150 μg/kg of body weight, in particular 0.5–100 μg/kg, and the unit doses used are about 0.005 μg–2 mg (per patient), the precise amount depending on the age, weight and condition of the patient or animal and on the frequency and type of administration.

The addition of these compounds to whole blood leads to in vitro uses, such as, for example, in the storage of whole blood for use in heart/lung machines. The blood containing these compounds can also circulate through organs, for example, heart and kidneys, which were taken from a donor and are held ready for transplantation. The compounds according to the invention are also useful for the preparation of concentrates rich in blood platelets for use in thrombocytopenia, chemotherapy and radiation therapy. For in vitro applications, 0.01–1.0 μg/ml of whole blood are used.

In particular, compounds of the formula I can also be used as hypotensive agents for lowering the blood pressure in mammals including humans. For this purpose, they are administered orally in doses of about 1.5 μg–1.5 mg/kg, preferably 5 μg–1 mg/kg, of body weight per day or as a unit dose of about 50 μg–20 mg (per patient) or by intravenous infusion at a rate of about 0.001 to about 1 μg/kg of body weight per minute, or in one or several doses of about 1.5 to 150 μg/kg of body weight per day.

The prostaglandin derivatives can also be used in mammals including humans as well as certain domestic animals, for example dogs and pigs, for lowering and controlling excessive secretion of gastric juices, whereby gastro-intestinal ulceration is reduced or prevented and the healing of such ulcers, if already present, can be accelerated. For this purpose, the compounds are injected intravenously, subcutaneously or intramuscularly, or they are infused. In this treatment, the dosage scheme for the prostaglandin depends on various factors including the type, age, weight, sex and medical condition of the patient, the dosage scheme of the anti-inflammatory synthetase inhibitor and the sensitivity of the patient to the synthetase inhibitor with respect to the gastro-intestinal action. Thus, for example, not every patient requiring an anti-inflammatory substance experiences the same unpleasant gastro-intestinal effects. Rather, the latter vary frequently in type and extent. The doctor or veterinary surgeon is therefore competent to establish whether the administration of the anti-inflammatory substance produces undesired gastro-intestinal effects in humans or animals and to prescribe the effective quantity of the prostaglandin, by means of which these effects can be largely eliminated.

Several representatives of these substances are suitable for the treatment of asthma. For example, they are useful as bronchodilators or as inhibitors of mediators, such as, for example, SRS-A and histamine, which are liberated from cells activated by an antigen/antibody complex. The compounds therefore counteract spasms and ease breathing in diseases such as bronchial asthma, bronchitis, bronchiectasis, pneumonia and emphysema. For these purposes, the compounds are administered in various dosage forms, for example orally in the form of tablets, capsules or liquids, rectally in the form of suppositories, parenterally, subcutaneously or intramuscularly, intravenous administration being preferred in emergency situations.

Effective administration in man is obtained by oral inhalation or by aerosol inhalation. Doses of 0.01–10 μg/kg of body weight, preferably 0.05–2 μg/kg, are administered once to four times daily, the precise amount depending on the age, weight and condition of the patient and on the frequency and type of administration.

EXAMPLE 1

2-Oxa-3-oxo-6-tetrahydropyranyloxymethyl-7-benzyloxybicyclo[3.3.0]octane 19.8 g of 55% strength NaH (0.454 mole) are introduced in portions, under argon and with cooling, into a solution of 89.44 g of 2-oxa-3-oxo-6-tetrahydropyranyloxymethyl-7-hydroxybicyclo[3.3.0]octane; (0.35 mole) in 125 ml of freshly distilled benzyl bromide (179.5 g, 1.05 moles). After removal of the cooling bath, the batch heats up to 105° C. and becomes viscous. Heating at 120° C. is continued for a further hour with stirring, the solution becoming mobile again. After cooling, the mixture is diluted with 200 ml of ethyl acetate and filtered over Celite. (The residue is cautiously stirred into ethanol.) The filtrate is concentrated and the residue is distilled in vacuo. To remove the last remnants of benzyl bromide, the residue is taken up in 400 ml of ethyl acetate and 70 ml of triethylamine are added. The salts which have precipitated after cooling are filtered and the filtrate is concentrated. The residue is filtered over 3 times the amount of silica gel (developing solvent: cyclohexane/ethyl acetate 1:1).

Yield: 105 g (75%)

NMR (CDCl$_3$): δ ppm: 7.3, s, 5H (aryl H), 4.8–5.2, m, 1H (O=C—O—C—H) and 4.4–4.6, d (broad), 3H (aryl CH$_2$—O, O—CH—O)

IR (film): cm$^{-1}$: 3030–3050 (aromatic CH) and 1760 (lactone C=O)

Rf (ethyl acetate): 0.43

EXAMPLE 2

(1-Benzyloxy-2-tetrahydropyranyloxymethyl-4-hydroxycyclopent-3-yl)-acetamide 68.1 g of the lactone (0.196 mole) from Example 1 are treated in 250 ml of methanol and 200 ml of liquid ammonia for 16 hours at 100° C. in a shaking autoclave. The solvent is stripped off and the residue is filtered over 4 times the quantity of silica gel (developing solvent: ethyl acetate, followed by ethyl acetate/methanol).

Yield: 49.3 g (69%)

Melting point: 70°–76° C. (from ethyl acetate/cyclohexane)

NMR (CDCl$_3$): δ ppm: 7.3, s, 5H (aryl H), 5.4–6.3, m (broad), 2H (NH$_2$), 4.55, s, 2H (aryl CH$_2$—O) and 4.1–4.3, m, 1H (O—CH—O)

IR (KBr): cm$^{-1}$: 3050–3600 (broad, shoulder at 3200, OH, NH), 3000–3050 (aryl H) and 1670 (amide C=O)

Rf (ethyl acetate): 0.07

EXAMPLE 3

(3-Tetrahydropyranyloxymethyl-4-benzyloxycyclopentan-1-on-2-yl)-acetamide 70 ml of Jones solution containing 19.32 g (0.193 mole) of $CrO_3$ are added dropwise at $-20°$ to $-25°$ C. to a solution of 49.3 g (0.136 mole) of the alcohol of Example 2 in 350 ml of acetone. (Jones solution comprises 26.7 g of $CrO_3$, 23 ml of concentrated $H_2SO_4$, and 21 ml of $H_2O$ made up to 100 ml.) The solution is stirred for a further 2 hours at $-20°$ C., and an excess of i-propanol is then added at this temperature. The solution is neutralized with triethylamine, allowed to warm up to room temperature and filtered over Celite. The residue is washed thoroughly with acetone, the filtrate is concentrated almost to dryness and ethyl acetate is added to the residue. The organic phase is washed several times with half-saturated NaCl solution, and the combined aqueous phases are saturated with NaCl and extracted several times with ethyl acetate. The combined extracts are dried over $MgSO_4$, concentrated and filtered over a short column (5 times the quantity of silica gel, developing solvent: ethyl acetate).

Yield: 30 g (61.2%)

NMR ($CDCl_3$): δ ppm: 7.3, s, 5H (aryl H), 5.2-6.1, m, 2H ($NH_2$), 4.55, m, 3H (aryl $CH_2$—O, O—CH—O) and 3.25-4.2, m, 5H ($CH_2$—O)

IR (film): $cm^{-1}$: 3100-3600 (broad, shoulder at 3200, OH, NH), 3000-3100 (aryl H), 1750 (C=O in the five-membered ring) and 1675 (amide C=O)

Rf (ethyl acetate/methanol 1:1): 0.44

EXAMPLE 4

1-Hydroxy-2-aza-3-oxo-6-tetrahydropyranyloxymethyl-7-benzyloxybicyclo[3.3.0]octane 5.0 g of the ketoamide (Example 3) are dissolved in 10 ml of methanol and the solution is left to stand at room temperature. The course of the reaction is followed by thin-layer chromatography, and the solvent is stripped off after the reaction has ended.

Yield: 5.0 g (100%)

NMR ($CDCl_3$): δppm: 7.3, s, 5H (aryl H), 6.2-6.35, m, 1H (NH), 4.56, m, 3H (aryl $CH_2$—O, O—CH—O) and 3.25-4.2, m, 5H ($CH_2$—O)

IR (film): $cm^{-1}$: 3050-3600 (broad, shoulder at 3200, NH, OH) and 1680 (lactam C=O)

Rf (ethyl acetate/methanol 8:1): 0.35

EXAMPLE 5

1-Phenylthio-2-aza-3-oxo-6-tetrahydropyranyloxymethyl-7-benzyloxybicyclo[3.3.0]octane 29 g of the ketoamide (80.3 mmoles) (Example 3) and 9.35 g of thiophenol (85 mmoles) are dissolved, under argon, in 200 ml of pyridine/methylene chloride (1:1 by volume). 14.05 g of trimethylchlorosilane (129 mmoles, 16.4 ml) are added dropwise to this solution at room temperature. The solution is then boiled under reflux for a further 6 hours at a bath temperature of 70° C. After cooling, the pyridinium hydrochloride which has precipitated out is filtered off with suction and the filtrate is concentrated. The residue is taken up with ethyl acetate and the solution is washed with water. The aqueous phase is extracted another 3 times with ethyl acetate and the combined organic phases are dried over $MgSO_4$. After stripping off the solvent, a dark oil remains which can be further processed without additional purification.

Yield: 42.9 g (>100%)

NMR ($CDCl_3$): δppm: 7.2-7.5, m, 10H (aryl H), 6.15-6.4, m, 1H (NH), 4.35-4.6, m, 3H (aryl $CH_2$—O, O—CH—O) and 3.2-4.2, m, 5H ($CH_2$—O)

IR (film): $cm^{-1}$: 3200 (broad, NH), 3060 (aryl H) and 1680 (lactam C=O)

Rf (ethyl acetate/methanol 8:1): 0.58

The hydroxylactam (Example 4) or mixtures of hydroxylactam and ketoamide can also be converted to the thioether by the same procedure.

EXAMPLE 6

2-Aza-3-oxo-6-tetrahydropyranyloxymethyl-7-benzyloxybicyclo[3.3.0]octane 42.9 g of the crude thioether are treated, in 750 ml of t-butanol, with 200 g of Raney nickel for 30 minutes at 25° C. The supernatant solution is then filtered over Celite and the Raney nickel is boiled up several times with methanol. The filtrate is concentrated and the residue is filtered over a short (0.2-0.5 mm) silica gel column (developing solvent: ethyl acetate/methanol 2:1).

Yield: 20 g (95.2%)

NMR ($CDCl_3$): δppm: 7.2, s, 5H (aryl H), 6.85-7.2, m, 1H (NH) 4.35-4.55, m, 3H (aryl $CH_2$—O, O—CH—O) and 3.1-4.2, m, 6H ($CH_2$—O, O=C—N—C—H)

IR (film): $cm^{-1}$: 3200 (broad, NH) and 1680 (lactam C=O)

Rf (ethyl acetate/methanol 8:1): 0.27

EXAMPLE 7

2-Aza-3-oxo-6-tetrahydropyranyloxymethyl-7-hydroxybicyclo[3.3.0]octane 10.1 g of the benzyl ether (Example 6) (29.24 mmoles) are hydrogenated with 6 g of palladium-on-charcoal in 100 ml of ethyl acetate for 24 hours at room temperature under normal pressure. The catalyst is filtered off over Celite, the filtrate is concentrated and the residue is subjected to chromatography over silica gel.

Yield: 6.1 g (79.2%)

Melting point: 105°-108° C.

NMR ($CDCl_3$): δppm: 6.7-7.0, m, 1H (NH), 4.4-4.6, m, 1H (O—CH—O) and 3.2-4.2, m, 7H ($CH_2$—O, OH, O=C—N—C—H)

IR (KBr): $cm^{-1}$: 3500-3000 (broad, shoulder at 3200, NH, OH) and 1680 (lactam C=O)

Rf (ethyl acetate/methanol 8:1): 0.10

EXAMPLE 8

2-Aza-3-oxo-6-tetrahydropyranyloxymethyl-7-biphenylcarbonyloxybicyclo[3.3.0]octane 6 g of the alcohol (Example 7) (17.4 mmoles) are stirred with 4.33 g of p-phenyl-benzoic acid chloride (20 mmoles) in 50 ml of dry pyridine at room temperature. The pyridine is stripped off, the residue is taken up in ethyl acetate and the solution is washed with water. The organic phase is dried over $MgSO_4$, concentrated and crystallized from isopropanol.

Yield: 9.1 g (89%)

NMR ($CDCl_3$): δppm: 7.2-8.1, m, 9H (aryl H), 6.8-7.1, m, 1H (NH), 5.0-5.4, m, 1H (O=C—O—C—H), 4.35-4.55, m, 1H (O—CH—O) and 3.2-4.2, m, 5H ($CH_2$—O, O=C—N—C—H)

Melting point: 172°-175° C.
IR (KBr): cm$^{-1}$: 3200 (broad, NH), 1720 (aryl ester C=O) and 1680 (lactam C=O)
Rf (ethyl acetate/methanol 4:1): 0.45

EXAMPLE 9

2-Aza-3-oxo-6-hydroxymethyl-7-biphenylcarbonyloxybicyclo[3.3.0]octane 9 g of the THP ether of Example 8 (20.7 mmoles) are stirred overnight at room temperature with 0.3 g of p-toluenesulfonic acid in 30 ml of absolute methanol. The solution is neutralized with pyridine and concentrated in a rotary evaporator. The residue is crystallized from methylene chloride.
Yield: 6.35 g (87.4%)
Melting point: 70°-72° C.
NMR (CDCl$_3$): δppm: 7.2-8.1, m, 9H (aryl H), 6.8-7.05, m, 1H (NH), 5.0-5.4, m, 1H (O=C—O—C—H), 3.95-4.3, m, 1H (O=C—N—C—H), 3.75, s, 1H (OH) and 3.5, d, 2H (CH$_2$—O)
IR (KBr): cm$^{-1}$: 3600-3000 (broad, shoulder at 3200, NH, OH), 1720 (aryl ester C=O) and 1680 (lactam C=O)
Rf (ethyl acetate/methanol 4:1): 0.32

EXAMPLE 10

2-Aza-3-oxo-7-biphenylcarbonyloxybicyclo[3.3.0]octane-6-carbaldehyde 6 g of the alcohol (Example 9) (16.3 mmoles) are suspended in 30 ml of absolute methylene chloride and the suspension is added dropwise at 0° C. to a suspension of 35.13 g of pyridinium chlorochromate (163 mmoles) and 100 g of Celite in 150 ml of absolute methylene chloride. The suspension is allowed to warm up to room temperature and is stirred at room temperature until the alcohol has disappeared from the thin-layer chromatogram (developing solvent: ethyl acetate). 16 g of sodium bisulfate are then added to the suspension and stirring at room temperature is continued for 70 minutes. Subsequently the mixture is filtered with suction over a frit covered with magnesium sulfate. The filtrate is concentrated and the residue is filtered over a short column of silica gel.
Yield: 4.05 g (67.8%)
NMR (CDCl$_3$): δppm: 10.2, d, 1H (CHO), 7.3-8.3, m, 9H (aryl H), 6.5-6.7, m, 1H (NH), 4.9-5.2, m, 1H (O=C—O—CH) and 3.7-4.0, m, 1H (O=C—N—C—H)
IR (KBr): cm$^{-1}$: 3200 (broad, NH), 1740 (CHO), 1710 (aryl ester C=O) and 1660 (lactam C=O)
Rf (ethyl acetate/methanol 8:1): 0.27

EXAMPLE 11

2-Aza-3-oxo-6-(3-oxo-oct-1-enyl)-7-biphenylcarbonyloxybicyclo[3.3.0]octane 22 mg of 55% NaH dispersion are initially introduced in 4 ml of dry DME and 111 mg of dimethyl 2-oxoheptylphosphonate (0.5 mmole) are added dropwise. A white precipitate forms. 150 mg of the aldehyde (0.5 mmole) (Example 10) in 3 ml of DME are added dropwise to this suspension. A part of the precipitate dissolves. The solution is left to stand overnight at room temperature. The solvent is stripped off and the residue is taken up in ethyl acetate. After adding water, the mixture is acidified to pH 4-5 with acetic acid, the organic phase is separated off and the aqueous phase is extracted a further 3 times with ethyl acetate. The combined extracts are dried over MgSO$_4$ and concentrated. A solid residue remains.
Yield: 136 mg (72%)
Melting point: 155° C. (from ethyl acetate/ether)
NMR (CDCl$_3$): δppm: 7.2-8.1, m, 9H (aryl H), 6.0-7.0, m, 2H (—C=C—H), 5.75, s (broad), 1H (NH), 5.1-5.4, m, 1H (O=C—O—C—H) and 4.0-4.45, m, 1H (O=C—N—C—H)
IR (KBr): cm$^{-1}$: 3200 (NH), 1715 (aryl ester), 1690 (lactam and enone C=O), 1630 (enone C=C) and 1610 (aryl C=C)
Rf (ethyl acetate/methanol 8:1): 0.49

Analogously to Example 11, the following enones of the general formula XV can also be prepared by reacting the aldehyde (Example 10) with phosphonates of the general formula XIV.

| Example No. | R$^3$ = | NMR data (δ ppm) |
|---|---|---|
| 11 a | (isopropyl-O-CH$_2$-) | 7.2-8.1, m, 9H (aryl H), 6.05-7.0, m, 2H (H—C=C—H), 5.8-5.9, m, 1H (NH), 5.15-5.14, m, 1H (O=C—O—C—H) 4.0-4.4, m, 1H (O=C—N—C—H, 3.5, q, 2H (O—CH$_2$—CH$_3$), 1.15, t, 3H (CH$_2$—CH$_3$) and 0.9, s, 6H (CH—(CH$_3$)) |
| 11 b | (thiophene-CH$_2$-O-CH$_2$-) | 6.0-8.15, m, 15H (aryl H, thiophene H, H—C=C—H, NH), 5.1-5.4, m, 1H (O=C—O—C—H), 4.0-4.4, m, 1H (O=C—N—C—H) and 3.9, d, 2H (CH$_2$—O—thiophene) |
| 11 c | F (fluoropentyl) | 7.1-8.05, m, 9H (aryl H) 6.05-7.0, m, 2H (H—C=C—H), 5.9-6.0, m, 1H (NH), 5.15-5.4, m, 1H (O=C—O—C—H), 4.0-4.4, m, 1H (O=C—N—C—H) and 0.9, t, 3H (CH$_2$—CH$_3$) |
| 11 d | (phenyl) | 7.2-8.1, m, 9H (aryl H), 6.05-7.05, m, 2H (H—C=C—H), 6.0, s (broad), 1H (NH), 5.2-5.4, m, 1H (O=C—O—C—H) and 4.0-4.4, m, 1H (O=C—N—C—H) |
| 11 e | (thiophene-CH$_2$-) | 6.05-8.15, m, 14H (aryl H, thiophene H, H—C=C—H), 6.2, s (broad), 1H (NH), 5.2-5.45 m, 1H (O=C—OCH) 4.0-4.4, m, 1H (O=C—N—C—H) and 2.8, s (broad), 4H (thiophene-CH$_2$—CH$_2$) |
| 11 f | (chlorophenyl-O-CH$_2$-) | 7.0-8.6, m, 13H (aryl H), 6.1, s(broad), 1H (NH), 5.2-5.4, m, 3H (O=C—O—C—H, aryl—O—CH$_2$) and 4.0-4.4, m, 1H (O=C—N—C—H) |

EXAMPLE 12

2-Aza-3-oxo-6-(3-(R,S)-hydroxy-oct-1-enyl)-7-biphenylcarbonyloxybicyclo[3.3.0]octane 61 mg of the enone (0.137 mmole) (Example 11) in 2 ml of DME are added dropwise, at 0° C., to a solution of 22 mg of ZnBH$_4$ (0.274 mmole) (prepared from 37 mg of ZnCl$_2$ and 10.4 mg of NaBH$_4$=0.274 mmole of each) in 5 ml of dry DME. The solution is stirred for 1 further hour at room temperature. After concentrating, the residue is taken up in ethyl acetate and water is added. After acidification to pH 3–4, the organic phase is separated off, and the aqueous phase is extracted twice more with ethyl acetate. The combined organic phases are dried over MgSO₄ and concentrated. The remaining solid is crystallized from ethyl acetate.

Yield: 50 mg (81.6%)

NMR (CDCl₃): δppm: 7.3–8.1, m, 9H (aryl H), 5.5–5.7, m, 3H (H—C=C—H, NH), 5.0–5.4, m, 1H (O=C—O—C—H) and 3.9–4.4, m, 2H (O=C—N—C—H, CH—OH)

IR (KBr): cm⁻¹: 3400 (broad, OH), 3200 (broad, NH), 1720 (aryl ester C=O), 1685 (lactam C=O) and 1615 (aromatic C=C)

Melting point: 177° C. (ethyl acetate)

Rf (ethyl acetate/methanol 8:1): 0.35 (β-isomer), 0.28 (α-isomer)

Analogously to Example 12, the compounds 12 a–12 f (formula XVI) can be prepared by reduction from the compounds of Examples 11 a–11 f.

| Example 12 | R³ | Rf values (β/α) (ethyl acetate/methanol 8:1) |
|---|---|---|
| (a) |  | 0.32/0.26 |
| (b) | 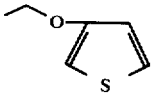 | 0.35/0.30 |
| (c) |  | 0.29/0.27 |
| (d) |  | 0.30/0.27 |
| (e) |  | 0.31/0.30 |
| (f) | 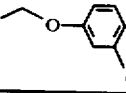 | 0.33/0.29 |

EXAMPLE 13

2-Aza-3-oxo-6-(3-(R,S)-biphenylcarbonyloxy-oct-1-enyl)-7-biphenylcarbonyloxybicyclo[3.3.0]octane 46 mg of the alcohol (0.103 mmole) (Example 12) and 24 mg of p-phenylbenzoyl chloride (0.110 mmole) are stirred overnight at room temperature in 1 ml of dry pyridine. The pyridine is stripped off and the residue is taken up in ethyl acetate. After extraction with water and drying over MgSO₄, the solution is concentrated. The residue is subjected to chromatography on silica gel (developing solvent: ethyl acetate).

Yield: 56 mg (87%)

Melting point: 132°–133° C. (ethyl acetate/hexane)

NMR (CDCl₃): δ ppm: 7.2–8.1, m, 18H (aryl H), 5.95, s (broad), 1H (NH), 5.55–5.7, m, 2H (H—C=C—H), 4.9–5.55, m, 2H (O=C—O—C—H) and 3.9–4.35, m, 1H (O=C—N—C—H)

IR (KBr): cm⁻¹: 3200 (broad, NH), 1715 (aryl ester C=O), 1690 (shoulder, lactam C=O) and 1615 (aromatic C=C)

Rf (ethyl acetate): 0.29

Analogously to Example 13, the diesters XVII (R⁴ and R⁵=biphenylcarbonyl) can be prepared from the compounds of Examples 12a–12f by esterification.

| Example 13 | R³ | Rf values (ethyl acetate) |
|---|---|---|
| (a) | 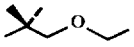 | 0.31 |
| (b) | 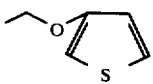 | 0.33 |
| (c) | 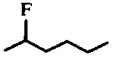 | 0.30 |
| (d) |  | 0.32 |
| (e) | 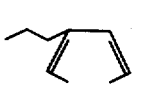 | 0.32 |
| (f) | 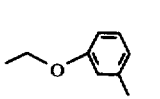 | 0.34 |

EXAMPLE 14

2-Aza-3-thio-6-(3-(R,S)-biphenylcarbonyloxy-oct-1-enyl)-7-biphenylcarbonyloxybicyclo[3,3.0]octane 36 mg of the lactam (0.057 mmole) (Example 13) are heated with 65 mg of the P₂S₅/pyridine complex (0.085 mmole) in 1 ml of dry pyridine to 80° C. for 3 hours. The solution is concentrated and the residue is taken up in ethyl acetate. The solution is washed twice with half-saturated NaCl solution, and the aqueous phase is saturated with NaCl and extracted a further 3 times with ethyl acetate. The combined organic phases are dried over MgSO₄ and concentrated, and the remaining oil is filtered over a silica gel column (developing solvent: ethyl acetate).

Yield: 30 mg (81.3%)

NMR (CDCl₃): δ ppm: 7.15–8.2, m, 18H (aryl H), 5.55–5.8, m, 2H (H—C=C—H), 5.0–5.55, m, 2H (O=C—O—C—H) and 4.2–4.6, m, 1H (O=C—N—C—H)

IR (film): cm⁻¹: 3300, 3150 (NH), 3030, 3060, (aryl CH), 1715 (aryl ester C=O), 1610 (aromatic C=C) and 1510 (R—NH—C=S)

Rf (cyclohexane/ethyl acetate 1:1): 0.37 (β-isomer), 0.30 (α-isomer)

Analogously to Example 14, the thiolactams XVIII (R⁴ and R⁵=biphenylcarbonyl) can be prepared from the compounds of Examples 13a–13f.

| Example 14 | R³ | Rf values (β/α) (ethyl acetate/cyclohexane 1:1) |
|---|---|---|
| (a) | 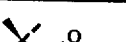 | 0.32/0.26 |

| Example 14 | R³ | Rf values (β/α) (ethyl acetate/ cyclohexane 1:1) |
|---|---|---|
| (b) | ethoxy-thiophene | 0.34/0.29 |
| (c) | CH(F)-propyl | 0.35/0.30 |
| (d) | cyclopentyl-H | 0.34/0.28 |
| (e) | CH₂-thiophene | 0.36/0.30 |
| (f) | ethoxy-chlorophenyl | 0.35/0.30 |

EXAMPLE 15

2-Aza-3-(1-thia-4-carboxyethylbut-1-yl)-6-(3-(R,S)-biphenylcarbonyloxy-oct-1-enyl)-7-biphenylcarbonyloxybicyclo[3.3.0]oct-2-ene 2 mg of 55% NaH dispersion (=1.1 mg of NaH, 0.046 mmole) are initially introduced in 0.5 ml of dry DME. At room temperature, 28 mg of the thiolactam (0.044 mmole) (Example 14) in 0.5 ml of DME are added dropwise and the mixture is stirred until the evolution of hydrogen has ceased. Subsequently, 9 mg of bromobutyric acid ester (0.046 mmole, 6.7 μl) are added dropwise and the mixture is stirred overnight at room temperature. The solvent is stripped off and the residue is subjected to chromatography over silica gel (developing solvent: ethyl acetate/cyclohexane 1:1).

Yield: 22.8 mg (69.2%)

NMR (CDCl₃): δ ppm: 7.6–8.1, m, 18H (aryl H), 5.5–5.7, m, 2H (H—C=C—H), 4.75–5.5, 2H (O=C—O—C—H), 4.25–4.75, m, 1H (S—C=N—C—H), 4.05, q, 2H (J=7 Hz, O=C—O—CH₂) and 3.05, t, 2H (N=C—S—CH₂)

IR (film): cm⁻¹: 1730 (ester C=O) and 1600 (C=N)

Rf (ethyl acetate/cyclohexane 1:1): 0.46

Analogously to Example 15, the thiolactim ethers XX (R⁴ and R⁵=biphenylcarbonyl, Z=CO₂C₂H₅, Y=—(CH₂)₃—) can be prepared by alkylation from the compounds of Examples 14a–14f.

| Example 15 | R³ | Rf values (ethyl acetate/cyclohexane 1:1) |
|---|---|---|
| (a) | C(CH₃)₂-O-ethyl | 0.43 |
| (b) | ethoxy-thiophene | 0.45 |
| (c) | CH(F)-propyl | 0.44 |
| (d) | cyclopentyl-H | 0.42 |
| (e) | CH₂-thiophene | 0.46 |
| (f) | ethoxy-chlorophenyl | 0.42 |

EXAMPLE 16

2-Aza-3-(1-thia-4-carboxymethyl-but-1-yl)-6-(3-(R,S)-hydroxy-oct-1-enyl)-7-hydroxybicyclo[3.3.0]oct-2-ene 10 mg of the phenylbenzoic acid ester (0.0132 mmole) (Example 15) are stirred overnight at room temperature with 11 mg of potassium carbonate (0.08 mmole) in 0.5 ml of dry methanol. The solution is cooled to 0° C. and adjusted to pH 4–5 with saturated citric acid solution. The precipitate is filtered off with suction and the filtrate is concentrated after the removal of acid by saturated NaHCO₃ solution. The residue is taken up in ethyl acetate, NaCl solution is added, the organic phase is separated off and the aqueous phase is extracted with ethyl acetate. After drying and concentrating the organic phases, the residue is subjected to chromatography over silica gel (developing solvent: methylene chloride/methanol 10:1).

Yield: 4.4 mg (87.2%)

NMR (CDCl₃): δ ppm: 5.4–5.6, m, 2H (H—C=C—H), 4.3–4.55, m, 1H (S—C=N—C—H), 3.6–4.3, m, 2H (CH—OH), 3.6, s, 3H (COOCH₃) and 3.1, t, 2H (N=C—S—CH₂)

IR (film): cm⁻¹: 1720 (ester C=O) and 1600 (C=N)

Rf (methylene chloride/methanol 10:1): 0.69 (β-isomer), 0.52 (α-isomer)

Analogously to Example 16, the thiolactim ethers of the formula I (X=S, Y=—(CH₂)₃—, Z=CO₂CH₃) can be prepared by saponification from the compounds of Examples 15a–15f.

| Example 16 | R³ | Rf values (β/α) (methylene chloride/methanol 10:1) |
|---|---|---|
| (a) | C(CH₃)₂-O-ethyl | 0.35/0.21 (CH₂CH₂/CH₃OH 15:1) |
| (b) | ethoxy-thiophene | 0.65/0.50 |
| (c) | CH(F)-propyl | 0.60/0.44 |
| (d) | cyclopentyl-H | 0.62/0.46 |

| Example 16 | R³ | Rf values (β/α) (methylene chloride/methanol 10:1) |
|---|---|---|
| (e) | 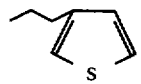 | 0.67/0.53 |
| (f) | 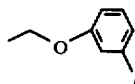 | 0.21/0.14 (cyclohexane/ethyl acetate 1:1) |

EXAMPLE 17

2-Aza-3-(1-thia-4-carboxyethylbut-3-en-1-yl)-6-(3-(R,S)-biphenylcarbonyloxy-oct-1-enyl)-7-biphenylcarbonyloxybicyclo[3.3.0]oct-2-ene 2 mg of 55% NaH dispersion (=1.1 mg of NaH, 0.046 mmole) are initially introduced in 0.5 ml of dry DME. At room temperature, 28 mg of the thiolactam (0.044 mmole) (Example 14) in 0.5 ml of DME are added dropwise and the mixture is stirred until the evolution of hydrogen has ceased. Subsequently, 8.9 mg of bromocrotonic acid ester (0.046 mmole) are added dropwise and the mixture is stirred overnight at room temperature. The solvent is stripped off and the residue is subjected to chromatography over silica gel (developing solvent: ethyl acetate/cyclohexane 1:1).

Yield: 18.4 mg (56%)

NMR (CDCl₃): δ ppm: 7.6–8.1, m, 18H (aryl H), 5.85–7.1, m, 2H (H—C═CH—CO₂—), 4.25–4.75, m, 1H (S—C═N—C—H), 3.7, s, 3H (CO₂CH₃) and 3.35, m, 2H (CH₂—S—C═N—)

IR (film): cm⁻¹: 1730 (ester C═O) and 1630 (C═N)

Rf (ethyl acetate/cyclohexane 1:1): 0.56

Analogously to Example 17, the thiolactim ethers XX (R⁴ and R⁵=biphenylcarbonyl, Z=CO₂C₂H₅, Y=C-H₂—CH═CH—) can be prepared by alkylation from the compounds of Examples 14a–14f.

| Example 17 | R³ | Rf values (cyclohexane/ethyl acetate 1:1) |
|---|---|---|
| (a) | 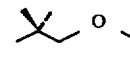 | 0.52 |
| (b) | 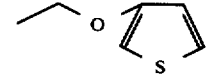 | 0.56 |
| (c) |  | 0.54 |
| (d) |  | 0.53 |
| (e) | 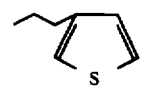 | 0.56 |
| (f) | 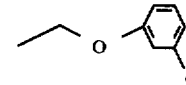 | 0.51 |

EXAMPLE 18

2-Aza-3-(1-thia-4-carboxymethylbut-3-en-1-yl)-6-(3-(R,S)-hydroxy-oct-1-enyl)-7-hydroxybicyclo[3.3.0]oct-2-ene 20 mg of the phenylbenzoic acid ester (0.027 mmole) (Example 17) are stirred overnight at room temperature with 22 mg of potassium carbonate (0.16 mmole) in 1 ml of dry methanol. The solution is cooled to 0° C. and adjusted to pH 4–5 with saturated citric acid solution. The precipitate is filtered off with suction and the filtrate is concentrated after the removal of acid with saturated NaHCO₃ solution. The residue is taken up in ethyl acetate, NaCl solution is added, the organic phase is separated, and the aqueous phase is extracted several times more with ethyl acetate. After the organic phases are dried and concentrated, the residue is subjected to chromatography over silica gel (developing solvent: methylene chloride/methanol 1:1).

Yield: 2.9 mg (56.3%)

NMR (CDCl₃): δ ppm: 5.8–7.1, m, 2H (H—C═CH—CO₂CH₃), 5.5–5.7, m, 2H (H—C═C—H), 4.3–4.75, m, 1H (S—C═N—C—H), 3.6–4.3, m, 2H (CH—OH), 3.7, s, 3H (CO₂CH₃) and 3.35, m, 2H (CH₂—S—C═N—)

IR (film): cm⁻¹: 3500–3000 (broad, OH), 1730 (ester C═O) and 1600 (C═N)

Rf (methylene chloride/methanol 10:1): 0.70 (β-isomer), 0.61 (α-isomer)

Analogously to Example 18, the thiolactim ethers of the formula I (X=S, Y=—CH₂—CH═CH—, Z=CO₂CH₃) can be prepared by saponification from the compounds of Examples 17a–17f.

| Example 18 | R³ | Rf values (β/α) (methylene chloride/methanol 10:1) |
|---|---|---|
| (a) | 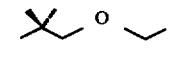 | 0.65/0.54 |
| (b) | 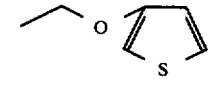 | 0.71/0.64 |
| (c) | 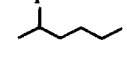 | 0.69/0.59 |
| (d) |  | 0.68/0.60 |
| (e) | 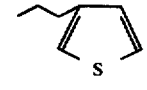 | 0.64/0.55 |

-continued

| Example 18 | R³ | Rf values (β/α) (methylene chloride/methanol 10:1) |
|---|---|---|
| (f) | [CH₂CH₂-O-C₆H₄-Cl structure] | 0.65/0.55 |

EXAMPLE 19

2-Aza-3-(1-oxa-4-carboxyethylbut-1-yl)-6-(3-(R,S)-biphenylcarbonyloxy-oct-1-enyl)-7-biphenylcarbonyloxybicyclo[3.3.0]oct-2-ene 72 mg of the lactam (0.114 mmole) (Example 13) and 43.7 mg of ethyl 4-bromobutyrate (0.228 mmole) are dissolved in 2 ml of dry xylene. The solution is heated to 60° C., 39.4 mg of silver oxide (0.17 mmole) are added and the mixture is heated to 140°-160° C. for 6 hours. After the mixture has cooled, 5 ml of diethyl ether are added, the mixture is filtered and the filtrate is concentrated. The residue is subjected to chromatography over silica gel (developing solvent: ethyl acetate/cyclohexane 1:1).

Yield: 59.3 mg (69.9%)

NMR (CDCl₃): δ ppm: 7.2–8.1, m, 18H (aryl H), 5.4–5.6, m, 2H (H—C=C—H), 4.6–5.4, m, 2H (O=C—O—D—H), 4.3, s (broad), 1H (O—C=N—C—H), 4.1 q (J=3.5 Hz), 2H (CO₂CH₂—) and 4.15, t (J=3 Hz), 2H (CH₂—O—C=N—)

IR (film): cm⁻¹: 1735 (ester C=O) and 1645 (C=N)

Rf (ethyl acetate/methanol 8:1): 0.79

Analogously to Example 19, the lactim ethers XXI (R⁴, R⁵=biphenylcarbonyl, Z=CO₂C₂H₅, Y=—(CH₂)₃—) can be prepared from the compounds of Examples 12a–12f.

| Example 19 | R³ | Rf value (ethyl acetate/methanol 8:1) |
|---|---|---|
| (a) | [isopropyl-O-ethyl] | 0.80 |
| (b) | [CH₂CH₂-O-thiophene] | 0.78 |
| (c) | [CHF(CH₂CH₂CH₃)] | 0.76 |
| (d) | [cyclopentyl-H] | 0.79 |
| (e) | [CH₂CH₂-thiophene] | 0.79 |
| (f) | [CH₂CH₂-O-C₆H₄-Cl] | 0.75 |

EXAMPLE 20

2-Aza-3-(1-oxa-4-carboxymethylbut-1-yl)-6-(3-(R,S)-hydroxy-oct-1-enyl)-7-hydroxybicyclo[3.3.0]oct-2-ene 29.3 mg of the phenylbenzoic acid ester (0.0396 mmole) (Example 19) are stirred overnight at room temperature with 33 mg of potassium carbonate (0.24 mmole) in 1.5 ml of dry methanol. The solution is cooled to 0° C. and adjusted to pH 4-5 with saturated citric acid solution. The precipitate is filtered off with suction and the filtrate is rendered neutral with saturated NaHCO₃ solution and concentrated. The residue is taken up in ethyl acetate, saturated NaCl solution is added and the organic phase is separated. The aqueous phase is extracted several times more with ethyl acetate and the combined extracts are dried over MgSO₄ and concentrated. The residue is subjected to chromatography over silica gel (developing solvent: ethyl acetate/methanol 8:1).

Yield: 10.9 mg (67.2%)

NMR (CDCl₃): δ ppm: 5.45–5.65, m, 2H (H—C=C—H), 3.9–4.45, m, 3H (CH₂—O—C=N), O—C=N—C—H), 3.6–3.9, m, 2H (CH—OH), and 3.8, s, 3H (CO₂CH₃)

IR (film): cm⁻¹: 3600–3000 (broad, OH), 1730 (ester C=O) and 1640 (C=N)

Rf (ethyl acetate/methanol 8:1): 0.09 (β-isomer), 0.06 (α-isomer)

Analogously to Example 20, the compounds of Examples 19a–19f can also be converted by saponification into the lactim ethers I (Z=CO₂CH₃, X=O, Y=—CH₂)₃—).

| Example 20 | R³ | Rf value (β/α) (ethyl acetate/methanol 8:1) |
|---|---|---|
| (a) | [isopropyl-O-ethyl] | 0.10/0.08 |
| (b) | [CH₂CH₂-O-thiophene] | 0.11/0.07 |
| (c) | [CHF(CH₂CH₂CH₃)] | 0.10/0.09 |
| (d) | [cyclopentyl-H] | 0.09/0.07 |
| (e) | [CH₂CH₂-thiophene] | 0.09/0.08 |
| (f) | [CH₂CH₂-O-C₆H₄-Cl] | 0.11/0.09 |

EXAMPLE 21

2-Aza-3-methylthio-6-(3-(R,S)-biphenylcarbonyloxy-oct-1-enyl)-7-biphenylcarbonyloxybicyclo[3.3.0]oct-2-ene 129 mg of the thiolactam (0.2 mmole) (Example 14) are dissolved in 1 ml of dry DME and added dropwise to a suspension of 8.7 mg of 55% strength sodium hydride dispersion (0.2 mmole=4.8 mg of NaH) in 5 ml of dry DME. The mixture is stirred at room temperature until the evolution of hydrogen has ceased. 31 mg of methyl iodide (0.22 mmole) are then added and the solution is warmed to 40° C. for 4 hours. The solvent is stripped off, and the residue is taken up in diethyl ether, washed with water, dried over $MgSO_4$ and concentrated.

Yield: 95.5 mg (72.4%)

NMR ($CDCl_3$): δ ppm: 7.6-8.1, m, 18H (aryl H), 5.5-5.7, m, 2H (H—C=C—H), 4.75-5.5, m, 3H (O=C—O—C—H, S—C=N—C—H) and 3.1, s, 3H ($CH_3$—S)

Rf (ethyl acetate/methanol 8:1): 0.83

The thiolactim ether is used without further purification for subsequent reactions.

Analogously to Example 21, the thiolactim ethers XXII ($R^7=CH_3$, $R^4$ and $R^5$=biphenylcarbonyl) can be prepared by methylation from the compounds of Examples 14a–14f.

| Example 21 | $R^3$ | Rf values (ethyl acetate/methanol 8:1) |
|---|---|---|
| (a) | | 0.85 |
| (b) | | 0.90 |
| (c) | | 0.87 |
| (d) | | 0.87 |
| (e) | | 0.84 |
| (f) | | 0.86 |

EXAMPLE 22

2-Aza-3-(1-aza-4-carboxybut-1-yl)-6-(3-(R,S)-biphenylcarbonyloxy-oct-1-enyl)-7-biphenylcarbonyloxybicyclo[3.3.0]oct-2-ene 77 mg of the thiolactim ether (0.12 mmole) (Example 21) are heated under reflux for 3 hours with 12.4 mg of γ-aminobutyric acid (0.12 mmole) in 1 ml of methanol. The solvent is stripped off and the residue is subjected to chromatography over silica gel (developing solvent: methylene chloride/methanol 5:1).

Yield: 79.5 mg (95%)

NMR ($CDCl_3$): δ ppm: 7.6-8.1, m, 18H (aryl H), 5.5-5.7, m, 3H (H—C=C—H, N=C—NH), 4.7-5.5, m, 2H (O=C—O—C—H), and 4.35, m, 1H (N—C=N—C—H)

IR (film): $cm^{-1}$: 2500-3500 (shoulder at 2980, $CO_2H$, CH, NH), 1680, 1565 (amidine) and 1400 (carboxylate)

Rf (methylene chloride/methanol 1:2): 0.35

Analogously to Example 22, the amidines XXIV (Z=$CO_2H$, $R^4$ and $R^5$=biphenylcarbonyl, Y=—($CH_2$)$_3$—) can be prepared from the compounds of Examples 21a–21f.

| Example 22 | $R^3$ | Rf values (methylene chloride/methanol 1:2) |
|---|---|---|
| (a) | | 0.38 |
| (b) | | 0.40 |
| (c) | | 0.34 |
| (d) | | 0.36 |
| (e) | | 0.37 |
| (f) | | 0.38 |

EXAMPLE 23

2-Aza-3-(4-carboxyethylanilino)-6-(3-(R,S)-biphenylcarbonyloxy-oct-1-enyl)-7-biphenylcarbonyloxybicyclo[3.3.0]oct-2-ene 77 mg of the thiolactim ether (0.12 mmole) (Example 21) are boiled under reflux for 3 hours with 19.8 mg of ethyl 4-aminobenzoate (0.12 mmole) in 1 ml methanol and 1 drop of glacial acetic acid. The solvent is stripped off and the residue is subjected to chromatography over silica gel (developing solvent: methylene chloride/methanol 8:1).

Yield: 87.6 mg (96.2%)

NMR $CDCl_3$): δ ppm: 6.8-8.1, m, 22H (aryl H), 6.0-6.4, m, 1H (N=C—N—H), 5.5-5.7, m, 2H (H—C=C—H), 4.7-5.5, m, 2H (O=C—O—C—H), 4.0-4.3, m, 1H (N—C=N—C—H), 4.25, q, 2H ($CO_2$—$CH_2$—) and 1.3, t, 3H ($CO_2CH_2CH_3$)

IR (film): $cm^{-1}$: 3400-3000 (broad, amidine NH), 1700 (ester C=O), 1640 and 1590 (amidine)

Rf (methanol/methylene chloride 1:8): 0.11

Analogously to Example 23, the amidines XXIV ($R^4$ and $R^5$=biphenylcarbonyl, Z=$CO_2C_2H_5$,

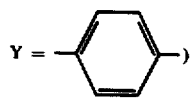

) can also be prepared from the compounds of Examples 21a–21f.

| Example 23 | $R^3$ | Rf value (methylene chloride/methanol 8:1) |
|---|---|---|
| (a) | | 0.13 |

| Example 23 | R³ | Rf value (methylene chloride/ methanol 8:1) |
|---|---|---|
| (b) | (ethyl-O-thiophene) | 0.15 |
| (c) | (CHF-propyl) | 0.14 |
| (d) | (cyclopentyl-H) | 0.13 |
| (e) | (CH₂-thiophene) | 0.15 |
| (f) | (ethyl-O-chlorophenyl) | 0.12 |

EXAMPLE 24

2-Aza-3-(1-aza-4-carboxybut-1-yl)-6-(3-(R,S)-hydroxy-oct-1-enyl)-7-hydroxybicyclo[3.3.0]oct-2-ene 71 mg of the diester (0.1 mmole) (Example 22) are stirred at room temperature for 2 hours with 12.8 mg of potassium carbonate (0.1 mmole) in 1 ml of absolute methanol. After neutralization with hydrochloric acid, 15 ml of ethyl acetate are added and the organic phase is separated and washed with water. The aqueous phase is saturated with sodium chloride and extracted several times with ethyl acetate. The combined organic phases are dried over MgSO₄ and, after filtering off the drying agent, are concentrated. The residue is subjected to chromatography over silica gel (developing solvent: methylene chloride/methanol 1:1).

Yield: 25.3 mg (72.2%)

NMR (CDCl₃): δ ppm: 5.45-5.7, m, 2H (H—C=C—H), 4.2-4.4, m, 1H (N—C=N—C—H) and 3.6-4.2, m, 2H (CH—OH)

IR (film): cm⁻¹: 2500-3500 (broad, CO₂H, CH, NH), 1685, 1560 (amidine) and 1410 (carboxylate)

Rf (methylene chloride/methanol 1:2): 0.20 (β-isomer), 0.17 (α-isomer)

Analogously to Example 24, the compounds of Examples 22a–22f can also be saponified to give amidines of the formula I (X=NH, Y=—(CH₂)₃—, Z=CO₂H).

| Example 24 | R³ | Rf value (β/α) (methylene chloride/ methanol 1:2) |
|---|---|---|
| (a) | (t-Bu-O-ethyl) | 0.21/0.19 |
| (b) | (ethyl-O-thiophene) | 0.23/0.20 |
| (c) | (CHF-propyl) | 0.22/0.20 |
| (d) | (cyclopentyl-H) | 0.21/0.20 |
| (e) | (CH₂-thiophene) | 0.22/0.20 |
| (f) | (ethyl-O-chlorophenyl) | 0.20/0.18 |

EXAMPLE 25

2-Aza-3-(4-carboxymethylanilino)-6-(3-(R,S)-hydroxy-oct-1-enyl)-7-hydroxybicyclo[3.3.0]oct-2-ene 79 mg of the diester (Example 23) (0.11 mmole) are stirred at room temperature for 2 hours with 14.1 mg of potassium carbonate (0.11 mmole) in 1 ml of dry methanol. After neutralization with hydrochloric acid, 15 ml of ethyl acetate are added and the organic phase is separated off and washed with water. The aqueous phase is saturated with sodium chloride and extracted several times with ethyl acetate. The combined organic phases are dried over MgSO₄ and, after filtration, are concentrated. The residue is subjected to chromatography over silica gel (developing solvent: methylene chloride/methanol 3:1).

Yield: 33.3 mg (75.4%)

NMR (CDCl₃): δ ppm: 7.8, 6.9, d (J=8 Hz), 4H (aryl H), 6.0-6.4, m, 1H (N=C—N—H), 5.5-5.7, m, 2H (H—C=C—H), 4.2-4.4, m, 1H (N—C=N—C—H), 3.6-4.2, m, 2H (CH—OH) and 3.7, s, 3H (CO₂CH₃)

IR (film): cm⁻¹: 3600-3000 (broad, OH, amidine NH), 1700 (ester C=O), 1640 and 1590 (amidine)

Rf (methylene chloride/methanol 3:1): 0.22 (β-isomer), 0.19 (α-isomer)

Analogously to Example 25, the compounds of Examples 23a–23f can also be saponified to give amidines of the formula I (X=NH, Y = 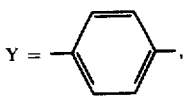,

Z=CO₂CH₃).

| Example 25 | R³ | Rf value (β/α) (methylene chloride/ methanol 3:1) |
|---|---|---|
| (a) | (t-Bu-O-ethyl) | 0.24/0.21 |
| (b) | (ethyl-O-thiophene) | 0.22/0.20 |
| (c) | (CHF-propyl) | 0.23/0.20 |

| Example 25 | R³ | Rf value (β/α) (methylene chloride/ methanol 3:1) |
|---|---|---|
| (d) |  | 0.22/0.20 |
| (e) | 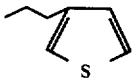 | 0.23/0.20 |
| (f) |  | 0.21/0.20 |

EXAMPLE 26

2-Aza-3-(4-hydroxybutylamino)-6-(3-(R,S)-biphenylcarbonyloxy-oct-1-enyl)-7-biphenylcarbonyloxybicyclo[3.3.0]oct-2-ene 105 mg of the thiolactim ether (0.16 mmole) (Example 21) are boiled under reflux for 5 hours with 14.6 mg of 4-aminobutanol (0.16 mmole) and 3 drops of glacial acetic acid in 1.5 ml of methanol. The solvent is stripped off and the residue is subjected to chromatography over silica gel (developing solvent: methylene chloride/methanol 3:1). P Yield: 94 mg (84.2%)

NMR (CDCl₃): δ ppm: 7.6–8.1, m, 18H (aryl H), 5.5–5.7, m, 3H (H—C=C—H, N=C—NH), 4.7–5.5, m, 2H (O=C—O—C—H) and 4.35, m, 1H (N—C=N—C—H)

IR (film): cm⁻¹: 3600–3000 (broad, OH, NH) and 1760 (ester C=O)

Rf (methylene chloride/methanol 1:3): 0.08

Analogously to Example 26, the amidines XXIV (Z=CH₂OH, R⁴ and R⁵=biphenylcarbonyl, Y=—(CH₂)₃—) can be prepared from the compounds of Examples 21a–21f.

| Example 26 | R³ | Rf values (methylene chloride/ methanol 1:3) |
|---|---|---|
| (a) | 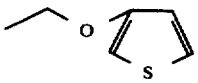 | 0.10 |
| (b) |  | 0.09 |
| (c) |  | 0.11 |
| (d) |  | 0.11 |
| (e) |  | 0.09 |
| (f) | 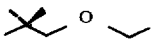 | 0.10 |

EXAMPLE 27

2-Aza-3-(4-hydroxybutylamino)-6-(3-(R,S)-hydroxy-oct-1-enyl)-7-hydroxybicyclo[3.3.0]oct-2-ene 90 mg of the diester (0.129 mmole) (Example 26) are stirred at room temperature for 2 hours with 16.5 mg of K₂CO₃ (0.129 mmole) in 1.3 ml of absolute methanol. After neutralization with hydrochloric acid, the solution is concentrated in a rotary evaporator. The residue is boiled up several times with ethyl acetate, the solvent is stripped off and the residue is subjected to chromatography over silica gel (developing solvent: methylene chloride/methanol 1:1).

Yield: 31.9 mg (73.4%)

NMR (CDCl₃): δppm: 5.45–5.7, m, 2H (H—C=C—H), 4.2–4.4, m, 1H (N—C=N—C—H) and 3.55–4.2, m, 4H (CH—OH)

IR (film): cm⁻¹: 3600–3000 (broad, OH, NH)

Rf (methylene chloride/methanol 1:5): 0.12

Analogously to Example 27, the compounds of Examples 26a–26f can also be saponified to give amidines of the general formula I (Z=CH₂OH, Y=—(CH₂)₃—).

| Example 27 | R³ | Rf values (methylene chloride/ methanol 1:1) |
|---|---|---|
| (a) | 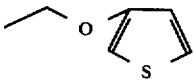 | 0.11 |
| (b) |  | 0.13 |
| (c) |  | 0.13 |
| (d) |  | 0.14 |
| (e) |  | 0.10 |
| (f) |  | 0.13 |

EXAMPLE 28

2-Aza-3(4-dimethylaminobutylamino)-6-(3-(R,S)-biphenylcarbonyloxy-oct-1-enyl)-7-biphenylcarbonyloxybicyclo[3.3.0]oct-2-ene 98 mg of the thiolactim ether (0.15 mmole ) (Example 21) are heated under reflux for 4 hours with 13.5 mg of dimethylaminobutylamine (0.15 mmole) and 3 drops of glacial acetic acid in 5 ml of methanol. The solvent is stripped off and the residue is subjected to chromatography over silica gel (developing solvent: methylene chloride/methanol 3:1).

Yield: 92.8 mg (89.3%)

NMR (CDCl₃): δppm: 7.6–8.1, m, 18H (aryl H), 5.5–5.7, m, 3H (H—C=C—H, N=C—NH), 4.7–5.5, m, 2H (O=C—O—C—H), 4.3, m, 1H (N—C=N—C—H) and 2.2, s, 6H (N—CH₃)

IR (film): cm⁻¹: 3200 (broad, NH) and 1710 (aryl ester C=O)

Rf (methylene chloride/methanol 1:3): 0.28

Analogously to Example 28, the amidines XXIV (Z=CH₂—N(CH₃)₂, R⁴ and R⁵=biphenylcarbonyl, Y=—(CH₂)₃—) can be prepared from the compounds of Examples 21a–21f.

| Example 28 | R³ | Rf values (methylene chloride/methanol 1:3) |
|---|---|---|
| (a) | | 0.25 |
| (b) | | 0.23 |
| (c) | | 0.26 |
| (d) | | 0.27 |
| (e) | | 0.24 |
| (f) | | 0.26 |

EXAMPLE 29

2-Aza-3-(4-dimethylaminobutylamino)-6-(3-(R,S)-hydroxy-oct-1-enyl)-7-hydroxybicyclo[3.3.0]oct-2-ene 90 mg of the diester (0.129 mmole) (Example 28) are stirred at room temperature for 2 hours with 16.5 mg of potassium carbonate (0.129 mmole) in 1.4 ml of absolute methanol. After neutralization with hydrochloric acid, the solvent is stripped off and the residue is boiled up several times with ethyl acetate. After the solvent has been stripped off, the residue is subjected to chromatography over silica gel (developing solvent: methylene chloride/methanol 1:1).

Yield: 32.4 mg (74.1%)

NMR (CDCl₃): δppm: 7.1, s (broad), 1H (NH), 5.5–5.7, m, 2H (H—C=C—H), 4.3, m, 1H (N—C=N—C—H) and 2.2, s, 6H (NCH₃)

IR (film): cm⁻¹: 3200 (broad, NH)

Rf (methylene chloride/methanol 1:3): 0.11

Analogously to Example 29, the compounds of Examples 28a–28f can also be saponified to give amidines of the formula I (Z=CH₂—N(CH₃)₂, Y=—(CH₂)₃—).

| Example 29 | R³ | Rf values (methylene chloride/methanol 1:3) |
|---|---|---|
| (a) | | 0.12 |
| (b) | | 0.14 |
| (c) | | 0.13 |
| (d) | | 0.13 |
| (e) | | 0.12 |
| (f) | | 0.10 |

We claim:
1. A compound of the formula

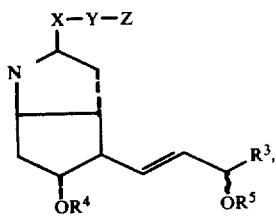

wherein
X is oxygen, sulfur, or —NH—;
Y is linear or branched alkylene having up to 8 carbon atoms, linear or branched alkenylene having 3 to 8 carbon atoms, phenylene, or is cycloaliphatic having 3 to 6 carbon atoms;
Z is —CO₂R¹, —CH₂OH, or —CH₂(R²)₂,
wherein
R¹ is hydrogen, linear or branched alkyl having up to 8 carbon atoms, linear or branched unsaturated aliphatic hydrocarbon having 3 to 6 carbon atoms, cycloaliphatic hydrocarbon having 3 to 7 carbon atoms, araliphatic hydrocarbon having 7 to 9 carbon atoms, a physiologically acceptable metal ion, NH₄⁺, or is a monoalkyl-, dialkyl-, trialkyl-, tetraalkyl-, or cycloalkyl-ammonium ion;
R² is hydrogen or is linear or branched aliphatic hydrocarbon having up to 5 carbon atoms, or the two R² groups taken together are —(CH₂)ₙ— wherein n is an integer from 3 to 6 inclusive;
R³ is phenyl or is phenyl mono-, di-, or tri-substituted by at least one member selected from the group consisting of halogen, trifluoromethyl, alkyl having 1 to 6 carbon atoms, and alkoxy having 1 to 6 carbon atoms, or R³ is cycloaliphatic having 3 to 8 carbon atoms, or is linear or branched alkyl having up to 8 carbon atoms, or is linear or branched unsaturated aliphatic hydrocarbon having 3 to 8 carbon atoms, or is such cycloaliphatic, alkyl, or unsaturated aliphatic hydrocarbon substituted by (a) linear or branched alkoxy having up to 6 carbon atoms or linear or branched alkenyloxy or alkynyloxy having 3 to 6 carbon atoms, (b) halogen, phenyl, α- or β-thienyl, or α- or β-furyl, or such phenyl, thienyl, or furyl mono-, di-, or tri-substituted by halogen, trifluoromethyl, alkyl having 1 to 6 carbon atoms, or alkoxy having 1 to 6 carbon atoms, or (c) phenoxy, α- or β-thienyloxy, or cycloalkoxy having 3 to 7 carbon atoms, or such phenoxy, thienyloxy, or cycloalkoxy mono-, di-, or tri-substituted by halogen, trifluoromethyl, alkyl having 1 to 6 carbon atoms, or alkoxy having 1 to 6 carbon atoms; and $R^4$ and $R^5$ are each hydrogen or an hydroxy-protective group which can readily be eliminated under neutral or basic conditions.

2. A pharmaceutical composition for the inhibition of blood platelet aggregation, comprising an amount of a compound as in claim 1 effective to inhibit blood platelet aggregation and a pharmaceutically acceptable carrier therefor.

3. A method for inhibiting blood platelet aggregation in a patient requiring such treatment, which method comprises systemically administering to said patient an amount of a compound as in claim 1 effective to inhibit blood platelet aggregation.

4. A pharmaceutical composition for the treatment of hypertension, comprising an amount of a compound as in claim 1 effective to reduce hypertension and a pharmaceutically acceptable carrier therefor.

5. A method for treating hypertension in a patient requiring such treatment, which method comprises orally administering to said patient an amount of a compound as in claim 1 effective to reduce hypertension.

6. A pharmaceutical composition for the treatment or prophylaxis of gastrointestinal ulcers, comprising an amount of a compound as in claim 1 effective to treat or prevent gastrointestinal ulcers and a pharmaceutically acceptable carrier therefor.

7. A method for the treatment or prophylaxis of gastrointestinal ulcers in a patient requiring such treatment, which method comprises infusing or intravenously, subcutaneously, or intramuscularly injecting into said patient an amount of a compound as in claim 1 effective to treat or prevent gastrointestinal ulcers.

8. A pharmaceutical composition for the treatment of asthma, comprising an amount of a compound as in claim 1 effective to counteract spasms and ease breathing and a pharmaceutically acceptable carrier therefor.

9. A method for treating asthma in a patient requiring such treatment, which method comprises orally, rectally, or parenterally administering to said patient an amount of a compound as in claim 1 effective to counteract spasms and ease breathing.

* * * * *